United States Patent [19]
VanderRoest et al.

[11] Patent Number: 6,118,002
[45] Date of Patent: Sep. 12, 2000

[54] PURIFICATION OF 1,2-DIHYDRO-6-ALKYL-2-OXO-5-(PYRIDINYL)-NICOTINONITRILES

[75] Inventors: James M. VanderRoest, South Haven; James J. Springer, Saugatuck; Richard S. Olsen, South Haven, all of Mich.

[73] Assignee: Wyckoff Chemical Company, Inc., South Haven, Mich.

[21] Appl. No.: 09/260,640

[22] Filed: Mar. 2, 1999

[51] Int. Cl.[7] ............ C07D 401/04; C07D 213/84; C07D 213/62
[52] U.S. Cl. ............ 546/257; 546/288; 546/298
[58] Field of Search .................... 546/288, 257, 546/298

[56] References Cited

U.S. PATENT DOCUMENTS

| | | | |
|---|---|---|---|
| 4,313,951 | 2/1982 | Lesher et al. | 514/334 |
| 4,347,363 | 8/1982 | Singh | 546/249 |
| 4,413,127 | 11/1983 | Singh | 546/249 |
| 4,417,054 | 11/1983 | Gelotte | 546/340 |
| 4,469,871 | 9/1984 | Gelotte | 546/249 |
| 4,681,944 | 7/1987 | Ippolito et al. | 546/340 |

*Primary Examiner*—Alan L. Rotman
*Attorney, Agent, or Firm*—Baker & Daniels

[57] ABSTRACT

The present invention comprises a process for preparing essentially pure 1,2-dihydro-6-alkyl-2-oxo-5-(pyridinyl)-nicotinonitriles from a crude reaction mixture containing the corresponding amide as an impurity. By "essentially pure" is meant a level of purity acceptable for orally administered pharmaceutical products, usually less than 0.1% of any single impurity. At least a stoichiometric amount of an acylating agent is reacted with the crude reaction mixture, and thereafter recovering essentially pure 1,2-dihydro-6-alkyl-2-oxo 5-(pyridinyl)-nicotinonitrile.

5 Claims, No Drawings

PURIFICATION OF 1,2-DIHYDRO-6-ALKYL-2-OXO-5-(PYRIDINYL)-NICOTINONITRILES

BACKGROUND OF THE INVENTION

This invention relates to a process for preparing 1,2-dihydro-6-alkyl-2-oxo-5-(pyridinyl)-nicotinonitriles (I) essentially free of the corresponding amide impurity. Compounds of the type described are known in the art to be useful as cardiotonic agents.

Prior art processes for preparation of such compounds are often burdened by co-production of impurities that require unusual measures to achieve purity levels suitable for pharmaceutical applications. Purification of such compounds to meet pharmaceutical specifications requiring exceptionally high purity is difficult even in the laboratory and more so in manufacture of commercial quantities. Indeed, even prior successful purification procedures require numerous time and yield-consuming cycles of recrystallization.

Illustrative of the preparation of compounds (I) are those in U.S. Pat. Nos. 4,313,951, issued Feb. 2, 1982, 4,347,363, issued Aug. 31, 1982, and 4,469,871, issued Sep. 4, 1984. The present invention provides a method of purification of 1,2-dihydro-6-alkyl-2-oxo-5-(pyridinyl)-nicotinonitriles using significantly fewer cycles of recovery than are expected from processes in the art.

Derivatization is a well-known concept for converting impurities in a crude mixture to fractions that may be cleared by further treatment to separate these fractions from the product to be purified. While easily stated as a procedure, the derivatizing agent must be selected with great care. The agent should be essentially unreactive with the desired end product but quantitatively reactive with the impurity. The derivatized impurities must have sufficiently high solubility differentiation against the desired product to yield a purified product requiring few cycles of fractional removal.

SUMMARY OF THE INVENTION

The present invention comprises a process for preparing essentially pure 1,2-dihydro-6-alkyl-2-oxo-5-(pyridinyl)-nicotinonitriles from a crude reaction mixture containing the corresponding amide as an impurity. By "essentially pure" is meant a level of purity acceptable for orally-administered pharmaceutical products, usually less than 0.1% of any single impurity. At least a stoichiometric amount of an acylating agent is reacted with the crude reaction mixture, and thereafter recovering essentially pure 1,2-dihydro-6-alkyl-2-oxo-5-(pyridinyl)-nicotinonitrile. The purified compounds have the following structure:

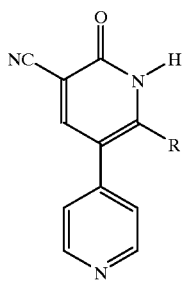

(I)

wherein R is hydrogen or lower alkyl.

DETAILED DESCRIPTION

The selected synthesis route for Compounds (I) presented the corresponding amide as the primary impurity to be removed. Compounds (I) exist as tautomers, in which one tautomer is always a phenol. Unfortunately, such compounds are well known to react with electrophilic agents. Moreover, it was not known whether the amide impurity would be derivatized by electrophilic agents or what the relative rates of derivatization might be. It was therefore unexpected to find in representative tests that Compounds (I) were unaffected but the amide was derivatized by acylating agents. Finally, the derivatized impurity was found to have highly differentiated solubility that facilitated separation and recovery by easy recrystallization. The success of the purification protocol employed herein and described below is ultimately dependent on these decisive solubility differentials, which are highly unpredictable, as well as the surprising stability of Compounds (1) against acylating compounds.

At least a stoichiometric amount of an acylating agent, based on weight of crude (I), is added to the crude reaction mixture, and essentially pure (I) is recovered by standard methods. A liberal excess of acylating agent is favored for maximum effect in terms of speed and completeness of reaction but could conceivably be run with little or no excess of acylating agent relative to the impurity. For example, if analysis showed 3% impurity, at least 0.03 equivalents of acylating agent would be required. Any remaining agent is satisfactorily removed in recrystallization or by other recovery means. Among useful acylating agents are acyl anhydrides and acyl halides. Acetic anhydride is preferred.

In order to accelerate derivatization, a catalyst may be added. While purification may be carried to satisfactory levels without a catalyst, prolonged reaction times may be encountered. Accordingly, although virtually any electrophilic catalyst will speed this reaction, N,N-dimethylaminopyridine as an acylation catalyst is preferred.

In the derivatizing step, crude or partially purified (I) is suspended or dissolved in an organic solvent, such as toluene, methylene chloride or the preferred N-methylpyrrolidine. To the reaction mixture is added, in no specific order, the acylating agent, such as triethylamine or other amine bases, and N,N-dimethylaminopyridine, with stirring. Ambient to elevated temperatures of about 50° C. have produced satisfactory results. The process itself is fairly independent of the temperature range in terms of the ultimate level of purity obtained, although higher temperatures may accelerate derivatization.

Under the conditions described, derivatization is usually "complete" within about one hour. Thereafter, derivatization progresses asymptotically regardless of the presence or absence of a catalyst and the temperatures of the derivatizing reaction. Crystallization solvents shown to be suitable include toluene, methanol, ethanol, isopropyl acetate and combinations of the foregoing. Toluene/methanol is the preferred system.

EXAMPLE 1

1,2-dihydro-6-methyl-2-oxo-5-(4-pyridinyl)-nicotinonitrile (milrinone)

Crude milrinone (20.5 g.) was determined by chromatographic analysis to contain about 6% impurity. The crude milrinone was dissolved in 50 ml. of dichloromethane and treated with 14.9 g. of acetic anhydride and 29.5 g. of triethylamine and 100 mg. of N,N-dimethylaminopyridine. After stirring for 4 hours, the solution was transferred to a flask containing 25 g. of sodium bicarbonate in 300 ml. of water. The layers were separated and the organic layer washed three times with 300 mil. of water. The organic layer was concentrated in vacuo to provide a solid residue, which was slurried in 200 ml. of toluene and 600 ml. of methanol. The resulting slurry was treated with 0.4 g. of carbon. This mixture was heated to reflux and the carbon removed by filtration. On cooling the toluene/methanol system to less than 10° C., 8.6 g. of milrinone (42% yield) was isolated. Chromatographic analysis showed the milrinone isolate to contain no single impurity greater than 0.1%.

EXAMPLE 2

1,2-dihydro-6-methyl-2-oxo-5-(4-pyridinyl)-nicotinonitrile (milrinone)

Crude milrinone (14.2 g.) containing 3% amide impurity was dissolved in 115 ml. of n-methylpyrrolidine and treated with 10 g. of acetic anhydride, 20 g. of triethylamine, and 0.05 g. of N,N-dimethylaminopyridine. After stirring for 12 hours, the product was isolated on precipitation with 85 ml. of water to provide 14 g. of crude milrinone. To the crude milrinone was added 142 ml. of toluene, 423 ml. of methanol, 2 g. of carbon, and 1 g. of Celite (filter aid). The mixture was heated to reflux and the carbon and Celite subsequently removed by filtration. On cooling, 9 g. of milrinone was isolated and shown by chromatographic analysis to contain less than 0.1% of any single impurity.

In like manner, other compounds within structure (I) that include the corresponding amide as an impurity may be essentially cleared of the amide.

What is claimed is:

1. A process for preparing essentially pure 1,2-dihydro-6-alkyl-2-oxo-5-(pyridinyl)-nicotinonitriles from a crude reaction mixture containing the corresponding amide as an impurity, said purified product having the structure:

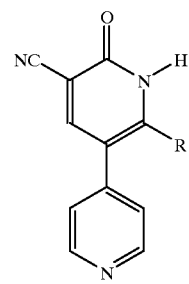

(I)

wherein R is hydrogen or lower alkyl, which comprises: reacting the crude reaction mixture with at least a stoichiometric amount of an acylating agent based on weight of the crude reaction mixture, and thereafter recovering essentially pure 1,2-dihydro-6-alkyl-2-oxo-5-(pyridinyl)-nicotinonitrile.

2. The process of claim 1 in which R is methyl.

3. The process of claim 1 in which the product to be purified is crude 1,2-dihydro-6-methyl-2-oxo-5-(4-pyridinyl)-nicotinonitrile that includes the corresponding amide as an impurity to be essentially removed.

4. The process of claim 3 in which the acylating agent is an acyl halide.

5. The process of claim 3 in which the acylating agent is acetic anhydride.

* * * * *